United States Patent [19]
Wilson

[11] Patent Number: 5,985,596
[45] Date of Patent: Nov. 16, 1999

[54] METHOD TO DETECT BACTERIA

[75] Inventor: Stuart Mark Wilson, London, United Kingdom

[73] Assignee: Biotec Laboratories Limited, United Kingdom

[21] Appl. No.: 09/077,992

[22] PCT Filed: Dec. 16, 1996

[86] PCT No.: PCT/GB96/03097

§ 371 Date: Jul. 27, 1998

§ 102(e) Date: Jul. 27, 1998

[87] PCT Pub. No.: WO97/22713

PCT Pub. Date: Jun. 26, 1997

[30] Foreign Application Priority Data

Dec. 15, 1995 [GB] United Kingdom .................... 9525661

[51] Int. Cl.$^6$ .............................. C12Q 1/06; C12Q 1/70; C12N 1/06; C12N 7/04
[52] U.S. Cl. ................... 435/39; 435/5; 435/236; 435/253.1; 435/259; 435/864; 435/866
[58] Field of Search ............................... 435/5, 39, 253.1, 435/259, 863, 864, 865, 866, 975, 236; 436/248.1

[56] References Cited

U.S. PATENT DOCUMENTS 5,498,525  3/1996  Rees et al. ................................ 435/29

FOREIGN PATENT DOCUMENTS

WO 92/02633  2/1992  WIPO .............................. C12Q 1/04

*Primary Examiner*—Kathleen K. Fonda
*Assistant Examiner*—Marjorie A. Moran
*Attorney, Agent, or Firm*—Hamilton, Brook, Smith & Reynolds, P.C.

[57] ABSTRACT

The present invention relates to a method for enhancing the time of response of an assay for a first bacterium, wherein: a) the first bacterium is exposed to infection by phage particles to which the first bacterium is permissive; b) the infected bacterium is treated to inactivate exogenous phage particles; c) the treated bacterium is cultivated in the presence of a second bacterium which is permissive to infection by the phage or its replicand and which has a doubling rate greater than the effective doubling rate of the first bacterium; and d) assessing the extent of plaque formation and/or of second bacterium growth in the cultivated second bacterium cells. The method can be used to assess the presence of first bacterium in a sample, notably where the first bacterium is a slow growing bacterium, such as *Mycobacterium tuberculosis,* where the method enables an operator to detect the presence of low amounts of the bacterium in sample within days instead of weeks as required by conventional cultivation techniques. The invention can also be used to assess the effect of a drug or other treatment on a bacterium or on a virus. The invention also provides a diagnostic kit for use in the method of the invention.

22 Claims, No Drawings

METHOD TO DETECT BACTERIA

This application is the US national stage entry under 35 U.S.C. 371 of international application PCT/GB96/03097, filed Dec. 16, 1996.

The present invention relates to a method, notably to a method for diagnosing the presence of a bacterium in a sample.

BACKGROUND TO THE INVENTION

It is common practice to propagate bacteria from a sample of a bodily fluid, such as sputum, on a suitable culture medium so as to be able to detect the colonies of bacteria on the culture medium either visually or using a test reagent or assay. Such a technique is applicable over a wide range of bacteria and has become widely accepted as a standard bacteria detection and diagnostic procedure. However, problems arise where the bacterium is a slow growing type where it may take several days or even weeks before adequate growth of the bacteria has taken place to be detectable. This is particularly the case with some Mycobacterium or Legionella species, where it can take up to four weeks or more to propagate detectable colonies of the bacteria. This enforces an unacceptable delay in confirming infection with the bacteria in patients and it would be desirable to provide a more rapid assessment of the presence and identity of the bacteria.

It has been proposed in PCT Application No WO92/02633 to prepare a sample of a viable bacterium and to infect that with a strain of a virus which is specific to that bacterium, such bacteria-infecting virus being denoted as bacteriophage or, more commonly, phage. Some of the phage particles infect the bacteria and replicate within the bacterial cell. Those phage particles which are not absorbed by the bacteria remain with the mother liquor or matrix of the carrier of the bacteria, typically a culture medium. If the infected sample is then treated, for example with heat and/or an acid to kill, or is washed with a surfactant to remove, the exposed, exogenous, phase particles, the exogenous phage particles are inactivated or removed. The infecting, endogenous, phage particles are not inactivated, since they are protected within the bacterial cell. The treated infected bacteria can then be cultured in the presence of further un-infected bacteria which are permissive to, that is can be infected by, the phage particles. The phage particles within the infected bacteria replicate causing the cell wall to rupture or lyse and release its load of replicated phage particles. This first generation of progeny phage particles infects other bacterial cells, causing successive cycles of infection replication and lysis. This gives an exponential increase in the number of phage particles in the culture medium. Either the reduced growth of the bacterial cells or the large number of replicated phage particles can be measured or observed, even where the initial number of infected bacterial cells was small, thus enhancing the sensitivity of the detection of the presence of the initial bacterial cells in the sample being assessed.

This modification enhances the sensitivity of detection of bacterial cells and has been used successfully in the detection of fast growing bacteria such as Salmonella spp. However, with slow growing bacteria such as Mycobacteria spp, we have found that the time taken for this procedure to give a detectable population of phage particles remains substantially the same as with other techniques and the procedure does not solve the time problem with such bacteria. The need still exists for a procedure which achieves rapid and accurate detection of slow growing bacteria.

We have devised a method by which slow growing bacteria can be rapidly detected, thus overcoming the problems in having to wait days or even weeks for such detection. The method can also be used to determine the sensitivity of given bacteria to antibiotic and other drugs and to determine whether a given antibiotic or drug is active against given bacteria or whether a given virucidal composition is effective against a given virus. Since the method can be performed using simple apparatus and by unskilled persons, the method readily lends itself to operation in third world countries where skilled microbiologists and complex apparatus may not be available.

SUMMARY OF THE INVENTION

Accordingly, from one aspect the present invention provides a method for detecting the presence of first bacterium in a sample, which method comprises the steps of:

a. infecting a viable sample of the first bacterium cells with a phage which is specific to that bacterium whereby at least some of the bacterium cells each absorb one or more of the phage particles;

b. in-activating or removing the phage particles which have not been absorbed by the bacterium cells;

c. cultivating the infected first bacterium cells in a medium containing at least one other second bacterium which has a reproduction rate greater than the reproduction rate of the said first bacterium whereby at least some of the said second bacterium cells become infected by phage particles released upon the lysis of said infected first bacterium cells, each of said infected bacterium cells acting as a source for further infection of a subsequent generation of the infection cycle; and d. monitoring either the population of replicated phage particles and/or the reduced growth of the said second bacterium in step c to determine the presence of said first bacterium cells in the sample under test.

Preferably, the cultivation and infection of the second bacterium is carried out to or near the steady state at which further bacterial cell growth and lysis substantially ceases. At this state, a substantially steady population of dead bacteria cells due to the activity of the phage particles is present in the cultivation medium. The areas of the cultivation medium in which phage replication has taken place can be detected visually as clear spots in the surrounding cultivation medium which is more cloudy, opaque or otherwise visually different due to the growth of viable bacteria. These areas of reduced bacterial growth due to phage activity are commonly termed plaques. Since the second bacterium reproduces at a greater rate than the first bacterium, the time taken for the initial infected first bacterium cells to produce detectable plaques is greatly reduced. This acceleration in the development of plaques does not occur when the same bacterium is used for the initial phage infection and for the subsequent cultivation steps.

Alternatively, the presence of replicated phage particles in the cultivation medium at the end of step c can be assessed using conventional phage assay techniques. This can be done in addition to or as an alternative to the determination of the existence of plaques as described above.

The method of the invention can thus be applied to the detection of slow growing bacteria in a sample, for example from a patient suspected of being infected with *Mycobacterium tuberculosis* or Legionnaires disease, where a conventional assessment would takes days or weeks to give any observable indication that such bacteria were present in the initial sample. In such a case, a proportion of the initial sample is infected with a phage specific to the expected bacterium and the phage particles are carried through the in-activation step b because they are protected by the bacterial cells which they have infected. These protected phage particles cause the development of phage or plaques in the environs of each infected first bacterium cell in the cultivation of the infected cells—step c. If none of the suspected bacteria were present in the sample, substantially no phage or plaques would be formed in step c and the cultivation medium would present a substantially uniform appearance.

The invention may also be carried out using a known bacterium which has been treated with an antibiotic or other drug under test to determine whether the antibiotic or drug has any bactericidal effect. In this case, the population of phage or plaques at the end of step c indicates the efficacy or otherwise of the antibiotic or drug in killing the initial bacterium. In a conventional test method, the antibiotic or drug would be applied to the bacterium and the number of dead cells would be a direct indication of the efficacy of the antibiotic or drug. However, it may be difficult to observe the individual dead cells except under a microscope. In this application of the invention, the treatment of the first bacterium with the antibiotic or drug, which may kill the first bacterium, is combined with infection of the remaining viable first bacterium with the phage particles to demonstrate how many of the first bacteria have escaped being killed by the antibiotic or drug.

In another application of the invention, a sample of a virus, or phage, is treated with a composition which has a virucidal or virus growth regulant effect. The treated phage is then used to infect a viable first bacterium which is permissive to that specific phage, that is the bacterium can be infected by that phage. The infected bacterium is then treated to in-activate the exogenous phage particles, that is those which do not infect the bacterium cells and remain exposed outside, or exogenous to, the cells. The in-activated infected first bacterium cell material is then cultured in the presence of a second, faster reproducing, bacterium to produce plaques where the phage particles in the infected first cells have replicated and lysed. If the initial treatment of the phage particles has been fully effective, no viable phage particles will be present when the first bacterium material is infected and, therefore, no viable phage particles will carry through to the cultivation in the presence of the second bacterium. Therefore, the second bacterium will reproduce to give a substantially uniform colour or opacity to the culture medium. If, however, the initial treatment of the phage particles was not fully effective, phage particles will be carried through to the cultivation of the second bacterium and will cause plaques, which can be detected visually.

For convenience, the invention will be described hereinafter in terms of the assessment of the presence of a slow growing Mycobacterium spp. The invention can be applied to bacteria from a wide range of aminal or vegetable hosts, but is of especial application in the detection of bacteria from mammal hosts and for convenience the invention will be described with especial reference to the assessment of such a slow growing bacterium in an initial sample of a bodily material from a human suspected of being infected with that bacterium.

The term slow growing bacterium is used herein to denote those bacteria which, under normal conditions of propagation at 37° C. in a culture medium comprising 90% v/v of the medium known as 7H9 and 10% v/v of the nutrient known as OADC, have an effective reproduction cycle as assessed by a doubling of the bacterial cell population (the effective doubling rate) in excess of 10 hours. Such bacteria would normally take in excess of 72 hours using a conventional cultivation technique to produce detectable phage population or plaques, or are diffiult to cultivate. Using the method of the invention, phage or plaques can usually be detected within 16 hours with such bacteria.

Typical slow growing bacteria include Mycobacterium spp, notably *Mycobacterium tuberculosis, Mycobacterium paratuberculosis and Mycobacterium avium;* Legionella spp, notably *Legionella pneumophila;* Helicobacter spp, notably *Helicobacter pylori;* Streptococcus spp, notably *Streptococcus adjacens;* and Rikettsia spp, notably *Rickettsia prowazekii.* The invention may also be applied to bacteria which, whilst having an instantaneous doubling rate of less than 10 hours, have an average effective doubling rate greater than this due to the difficulty with which they initially propagate, for example *Streptococcus defectens* and Extremophiles spp. The term slow growing bacteria is therefore used herein and in the claims to denote bacteria which are inherently slow propagators and bacteria which have a slow average propagation rate over a period of ten hours due to intermittent failure or interruptions in their propagation cycle.

Whilst the invention is of especial benefit in detecting such slow growing bacteria, the invention can be applied to any bacterium where it is desired to increase the speed of formation of a detectable phage population or plaques, for example in the detection of bacteria which have a doubling rate shorter than 10 hours, for example in the range 4 to 10 hours, in human samples, food products or in samples taken to determine bacterial infestations in kitchens and the like, so as to provide more rapid testing for bacteria than would be achieved using conventional bacterial cultivation techniques. For convenience, the invention will be described hereinafter in terms of the use of Mycobacterium tuberculosis as the first bacterium.

The first bacterium can be present in any suitable form of sample from the patient, eg. sputum or other mucal secretions. However, the invention can be applied to samples of other bodily materials, for example, blood, urine or stools, from humans, other mammals, such as horses, cattle, sheep and pigs, and samples from vegetable matter, for example leaf or root crops or fruit. For convenience, the invention will be described hereinafter in terms of testing a sample of sputum from a human patient.

Typically, the sample will exist as a freshly drawn fluid in which the bacterium is still viable. However, where the sample has been frozen or dried for storage and/or transport prior to testing, it will usually be desired to hold the sample in a suitable culture medium at about 20 to 55° C., preferably 37° C., to ensure that the bacteria are viable and capable of infection with phage particles in step b of the method of the invention. If desired, the initial sample can be treated, for example thinned with N-acetyl cysteine and/or treated with alkali, surfactant or an acid, to reduce the population of other bacteria which might interfere with the detection of the bacterium under assessment. Such pre-treatments can be carried out using conditions and techniques commonly used in the preparation of bacterial samples for assessment. However, the need to decontaminate the initial sample from other bacteria is reduced as compared with conventional methods for assessing slow growing bacteria, since the method of the invention is more rapid than conventional test methods and the effect of the other bacteria is less marked.

The initial sample contains the bacterium to be assessed in a viable state. This will usually be in a fluid or gel, eg.

agar, cultivation medium. However, the carrier medium could be a particulate solid or the pores of a foraminous material, such as a ceramic frit or a foamed plastic or a filter paper or the mesh apertures in a reticulate material, impregnated with a suitable nutrient composition. For convenience, the invention will be described hereinafter in terms of the use of a fluid carrier medium for the initial bacterium sample which is subsequently applied to a gel carrier medium.

The initial sample is infected with a suitable phage which is specific to the type of first bacterium under assessment and to the second bacterium in which the infected first bacterium is to be cultivated in step c of the method of the invention. The phage may be generically specific to the type of bacterium, so that the phage will infect a range of bacteria within a genus. However, it may be preferred to use a narrowly specific phage where a specific bacterium is to be assessed. If desired, the phage may be modified to increase the specificity of the phage, so as to reduce infection of other bacteria in the sample being assessed. Suitable phage modification can be achieved by known techniques, for example by genetic modification, having regard to the specific bacterium to be infected, for example as described in PCT Application No WO92/02633. Typical phage for present use include AG1, B1, $BG_1$, $BK_1$, C3, D29, D34, D56A, GS4E, HP1, L1, I3 and TM4. The optimum phage for present use will depend upon the first and second bacterium used, since the phage or its replicand produced upon lysis from a bacterial cell needs to be permissive to the bacteria used. Thus, where the presence of *Mycobacterium tuberculosis* is being assessed using *Mycobacterium smegmatis* as the second bacterium, the phage D29 is suitable; and where *Mycobacterium avium* is used, the phage TM4 is suitable.

The phage can be provided in the form of, for example, a cultivar in a fluid medium or can be provided in the form of freeze or spray dried particles. The phage is admixed with the viable bacterial sample using any appropriate technique and under any suitable conditions. Typically, the bacterial sample will be in the form of a fluid and the phage infection is applied in a fluid carrier to the bacterial sample.

It is preferred to allow the phage infection to proceed at temperatures of up to 55° C., notably at about 37° C., for from 10 minutes to 4 hours to allow infection of the majority of the bacterial cells with at least one phage particle each. However, excessive infection may so weaken the bacteria that they do not survive the in-activation of the non-absorbed phage particles using acid as described below. The optimum infection time for a given bacterium can be determined by simple trial and error tests or by microscopic examination of the infected bacteria, having regard to the conditions to be experienced in the subsequent stages of the method of the invention.

The infected bacterial sample is then treated to remove or in-activate any exogenous phage particles which have not been absorbed into the bacterial cells and which remain outside the bacterial cells and exposed to the conditions introduced during the in-activation stage—step b. For convenience, the term in-activation will be used herein to denote collectively any process which renders the non-absorbed phage particles substantially incapable of replication in the next step of the method of the invention. The term thus includes the physical separation or removal of the phage particles from the sample or the de-activation of the particles. This in-activation can be carried out using any suitable technique, for example those described in PCT Application No WO92/02633. Preferred techniques include washing and filtration of the infected sample to separate the exogenous phage particles physically from the infected bacterial cells; by treating the infected sample with an acid, surfactant or chemical to kill or render inactive the exogenous phage particles; or by preferentially absorbing the exogenous phage particles from the infected sample on a suitable substrate which can then be separated from the bacterial cells.

For convenience, the invention will be described hereinafter in terms of chemical or acid treatment of the mixture of infected bacterial cells and exogenous phage particles. Such treatment is preferably carried out using a mineral acid or a iron salt thereof, for example ferrous ammonium sulphate, or phosphoric or sulphuric acid; a $C_{1-4}$ aliphatic carboxylic acid, notably acetic acid, which may be diluted glacial acetic acid or vinegar; or an acidic buffer medium. The treatment achieves a pH value in the bacterial carrier medium which in-activates the phage used, but which does not kill the infected first bacterium. The optimum washing and pH conditions will depend upon the bacterium under assessment and can be determined by simple trial and error tests. Typically, the infected bacterial material is acidified and incubated at an elevated temperature, typically about 37° C., for sufficient time, typically about 15 minutes, and the pH is then adjusted to about neutrality by the addition of an alkali or base.

In an alternative technique, the exogenous phage is killed by the addition of a virucide to the infected bacterial material. The optimal virucide will depend upon the phage to be killed and the nature of the first bacterium and can readily be determined by simple trial and error tests. Thus, suitable virucides for present use where the first bacterium is *Mycobacterium tuberculosis* include iron salts of mineral acids, and unsaturated fatty acids and alcohols containing from 12 to 24 carbon atoms, optionally with actinic or other radiation, notably UV radiation at about 400 to 600 nm wave length.

After in-activation, the bacterial material contains viable first bacterial cells having inside at least some of them viable phage particles. This mixture is mixed with a cultivation mixture containing a second bacterium or mixture of bacteria. These second bacteria are characterised in that they are infectable by the phage particles within the cells of the first bacteria, that is they are permissive to the phage; and in that they propagate at a rate which is greater than the propagation rate of the first bacterium under assessment. It is preferred that the second bacterium has a doubling rate which is at least twice the doubling rate of the first bacterium. The optimal relative rate of propagation will depend upon the actual rate of propagation of the first bacterium, in that a high relative rate of propagation will be required with a very slow growing first bacterium if the time taken to produce a detectable phage population and/or reduced second bacterial growth areas or plaques is not to be excessive. Typically, the second bacterium will have a doubling rate of from 4 to 20 times that of the first bacterium. Thus, for the assessment of *Mycobacterium tuberculosis* in the initial sample, we have found that the use of *Mycobacterium smegmatis* as the second bacterium gives particularly rapid results. Other suitable second bacteria for present use include other Mycobacteria, for example *Mycobacterium aurum.*

If desired, the infected first bacterium can be allowed to stand after the in-activation step b to achieve at least one generation of replication and release of the phage particles from the infected cells, before admixture with the second bacterium. Such standing allows the replicated phage particles to be released from the infected bacterial cells so as to provide more sites of potential infection within the second bacterial cells which assists the detection of low numbers of viable first bacterium in the initial sample.

In step c of the method of the invention, the infected first bacterium is cultivated in the presence of the second, faster propagating bacterium. When the phage particles replicate within the infected first bacterium cells, they form a larger number of phage particles which are released from the infected cells as the cells lyse. Each released phage particle can infect an adjacent bacterial cell, which may be a first or second bacterium cell. Each of the phage particles in those newly infected bacterial cells can replicate and are released to infect further bacteria cells; and so on.

Cultivation of the mixture of first and second bacteria can be carried out using any appropriate techniques and conditions. Typically, the second bacteria will be used in the form of a cultivation in a fluid or gel medium which is mixed with the infected first bacteria. However, the second bacteria may be used in the form of a freeze or spray dried powder or as solid particles having the bacteria impregnated or coated thereon. For convenience, the invention will be described hereinafter in terms of the application of the second bacterium in an agar gel carrier to the infected first bacterium. The amount of the second bacterium added to the treated first bacterium sample can vary over wide ranges depending upon the expected amount of first bacterium cells in the sample and the desired time within which a result from the method of the invention is required. In general, it is preferred to provide a greater number of second bacterium cells, typically from 2 to 50 times, than the number of first bacterium cells so as to enhance the probability that a phage particle lysed from an infected first bacterium cell will infect a second bacterium cell rather than another first bacterium cell. The optimum ratio of first to second bacterium cells can readily be established by simple trial and error tests.

During the cultivation process, it is preferred that the cultivation medium change in some detectable way to reflect the presence of replicated phage particles, viable second bacteria or plaques of dead bacterial cells due to the action of the phage particles. Typically, growth of the second bacteria will cause cloudiness or colour in an agar cultivation medium and the phage particles and associated dead bacterial cells from which they have been released will result in less cloudy or clear spots, plaques, within the coloured or cloudy medium, so that the plaques can be detected and assessed visually. Alternatively, the areas of differential growth can be detected by differential staining using conventional staining techniques. Where the cultivation medium contains appropriate ingredients, the bacterial cells can release lumiphores when they lyse and these can be detected under UV radiation, for example as described in PCT Application WO92/02633. The increased numbers of replicated phage particles can also be detected by immunoassay techniques, for example ELISA, or another enzymatic technique.

The number of phage particles and/or of plaques gives an indication of the number of first bacterium cells present and hence the presence or otherwise of such cells in the initial sample to be assessed.

As indicated above, the method of the invention provides a rapid test for the presence of an expected bacterial strain in the initial sample from the patient. By suitable selection of the phage particles used to infect the first bacteria, the test can be made specific to a particular bacterium. Alternatively, the test can provide a broad indication as to the type of bacteria present in the initial sample. The method of the invention can thus be tailored to the results required. Since the results can be obtained in a matter of hours rather than days as hitherto required, it is practicable to carry out an initial general screen, followed by a specific test once the general type of bacterium present in the initial sample has been identified. Since the method of the invention can be carried out using simple cell culture techniques and the results can be assessed visually, the method of the invention can readily be used in third world countries where skilled labour and complex laboratory facilities may not be available.

The invention also provides a diagnostic test kit for use in the method of the invention to detect the presence or absence of a first bacterium in a sample, which kit comprises a source of a known phage infection for the first bacterium; a source of a viable second bacterium which has a doubling rate which is faster than that of the first bacterium and which is permissive to the phage particles to be released from the first bacterium infected by said phage infection. Preferably also, the kit comprises means for in-activating and/or removing the exogenous phage particles from first bacteria infected by said source of phage infection.

The invention will now be illustrated by the following examples in which all parts are given by weight unless stated otherwise.

EXAMPLE 1

The rationale of the invention was tested in a safe model system using slow growing vaccine strain BCG to represent the first bacterium which had a typical doubling time of at least 10 hours and fast growing *Mycobacterium smegmatis* as the second bacterium which had a typical doubling time of about 2 hours. This example combined liquid and solid agar steps and the exogenous phage were in-activated with acid.

Step 1. A colony of BCG from an agar-based media was grown in liquid culture in 7H9 plus 10% (v/v) OADC supplement (Difco) (referred to hereinafter as 7H9, OADC) at 37° C. for two weeks to yield a stock of cells which could be used in the detection assay. In the clinical situation these cells would originate directly from a clinical sample and would not require this pre-culture step. In the clinical situation the slow-growing cells would be *Mycobacterium tuberculosis*.

Step 2. The liquid culture containing the BCG cells was serially diluted and 10 $\mu$l of each dilution was mixed with 10 $\mu$l of 7H9, OADC containing $10^5$ D29 bacteriophage (phage). Controls samples were also set up containing:

a) no BCG, where 10 $\mu$l of media without any BCG was mixed with phage; and b) a heat-killed control where the BCG was killed by heating at 80° C. for 30 minutes before mixing with the phage.

Step 3. After incubation for 90 minutes at 37° C. exogenous phage particles were inactivated by addition of 20 $\mu$l of 1.2% (v/v) HCl.

Step 4. 20 $\mu$l of 22.2 mM NaOH was then added to neutralize the acidity.

Step 5. 10 $\mu$l of this solution was then spotted onto an agar plate containing 7H9, OADC, 5% (v/v) of a stationary phase *Mycobacterium smegmatis* culture and 1.5% Bactoagar (Difco)

Step 6. The plate was then incubated at 37° C. to allow the protected endogenous phage particles to replicate within the BCG cells. The replicated phage particles caused lysis of the BCG cells and were released. At least some of the released phage particles infected the *Mycobacterium smegmatis* and set up an infection cycle in these faster growing cells.

Step 7. After 16 hours the plates were then observed for clear areas of phage lysis or plaques among the cloudy growth of uninfected *Mycobaterium smegmatis* indicator cells. The results were recorded and are shown below:

| Sample | Extent of lysis |
| --- | --- |
| Undiluted BCG | + |
| $10^{-2}$ dilution | 10 plaques |
| $10^{-4}$ dilution | − |
| Heat Killed BCG | − |
| No BCG, phage only | − |

+ Individual plaques observed but too many to count
− no plaques

The heat killed BCG and phage only controls remained negative showing that live cells were required to provide the phage with protection from in-activation by acid. Live BCG was able to protect the phage, which infected and replicated inside the BCG cells. Upon lysis of the BCG cells, the replicated phage were released and at least some of the phage began a replication cycle in the rapid growing *Mycobacterium smegmatis* which yielded plaques after 16 hours of incubation. The highest dilution of BCG which showed lysis was $10^{-2}$ which, as the original BCG culture used was still in early log phase, represents approximately $10^3$ BCG colony forming units. This assay, therefore, has the potential to detect the presence of as few as $10^3$ live slow growing bacteria in a given sample. This sensitivity is higher than that stated for microscopy and about the same as the sensitivity of culture when the conventional methods are applied to the detection of Mycobacteria. However, the time taken to develop observable plaques was less than 24 hours as compared to the 4–6 weeks required for conventional culture techniques.

EXAMPLE 2

The procedure of Example 1 was repeated except that the assay was performed in a solid agar medium and exogenous phage were removed by washing rather than in-activated by acid treatment.

Step 1. Step 1 was performed as described in Example 1.

Step 2. Successive 10-fold dilutions of BCG culture were performed in 7H9, OADC. 10 μl of each dilution was spotted onto an agar plate (7H9, OADC, 1.5% Bactoagar). 10 μl of a heat killed BCG culture was also spotted onto a similar plate to provide a control test. The plates were held at 37° C.

Step 3. A piece of filter paper was wetted with 7H9, OADC, 3% milk powder, $10^6$ D29 bacteriophage per milliliter. This was laid on top of the spotted plates and incubated at 37° C. for 20 minutes to allow infection of the bacterial cells on the plates.

Step 4. A stack of five pieces of filter paper was placed on top of the phage soaked filter paper and exogenous phage removed from the environs of the infected cells by capillary action through the stack of filter paper.

Step 5. When the stack of filter paper was completely wetted all filter paper was removed from the agar surface and discarded.

Step 6. The infected cells were then stripped from the surface of the agar using a nitrocellulose filter. The nitrocellulose filter was placed on the agar, allowed to wet and then peeled off. This filter was then placed cell side down on an agar plate containing the rapid grower *Mycobacterium smegmatis* indicator cells (7H9, OADC, 5% (v/v) of a stationary phase *Mycobacterium smegmatis* culture, 1.5% Bactoagar).

Step 7. The plates from step 6 were incubated at 37° C. until plaques could be observed visually (about 16 hours) and the results were recorded.

| Sample | Extent of lysis |
| --- | --- |
| undiluted BCG | +++ |
| $10^{-1}$ dilution | +++ |
| $10^{-2}$ dilution | ++ |
| $10^{-3}$ dilution | + |
| $10^{-4}$ dilution | − |
| Heat Killed BCG | − |

+++ complete lysis of indicator cells (no cell growth)
++ plaques merged with some growth of indicator cells between plaques
+ Individual plaques observed but too many to count
− no plaques The heat killed control again remained negative showing that live cells were required to provide the phage with protection from removal by washing. Live BCG were able once again to protect the phage which infected and replicated inside the BCG cells. Upon lysis of the BCG cells the replicated phage were released and at least some of the phage began a replication cycle in the rapid grower *Mycobacterium smegmatis* which yielded plaques after 16 hours of incubation. The highest dilution of BCG which showed lysis was $10^{-3}$ which, as the original BCG culture was in the late log phase of growth, represents approximately $10^3$ BCG colony forming units. This assay in this format, therefore, has the potential to detect the presence of as few as $10^3$ live slow growing bacteria in a given sample.

EXAMPLE 3

This example demonstrates an alternative method for carrying out the bacterial assay.

Processing of sputum samples for the phage infection step:
The whole sputum sample is placed in a sterile 20 ml screw-capped glass bottle.
1. An equal volume of "Decontaminating Agent" is added to the sample to decontaminate and liquify the sample.
2. The diluted sample is mixed by inverting several times and the mixture is left to stand for 10 minutes to allow the sputum to liquify.
3. The sample is then centrifuged at 4000×g for 10 minutes to pellet the bacilli.
4. The resultant supernatant liquor is poured off into neat Hycolin disinfectant and disposed of.
5. The bacilli pellet is re-suspended in 20 mls of sterile distilled water.
6. The suspended bacilli mixture is centrifuged as in stage 4 to pellet the bacilli.
7. The bacilli pellet is then re-suspended in 1.0 ml of "Growth Media" and allowed to stand for 24 hours at 35–37° C. to provide the sample for the assay test.
8. Control samples are prepared by adding 1.0 ml of "Growth Media" to a fresh tube to provide a in-activation control sample; and by adding 1 drop of "Helper Cells" to 1.0 ml of "Growth Media" in a fresh tube to provide a positive control for the protection of endogenous phage.

Infection of the bacilli with bacteriophage:
9. Using a sterile pastette, 1 drop (50 μl) of "Bacteriophage" is added to each test sample, including the in-activation control sample. Mix by agitation and incubate 3.0 hours at 35–37° C. without shaking. The positive control for the protection of endogenous phage is not processed at this time.
10. 2.5 hours after adding bacteriophage to the samples, a pellet of *Mycobacterium smegmatis* is added to the positive control tube.

11. All the test and control samples are incubated for a total of 3 hours each. 2 Drops (100l) of "Inactivation Reagent" are added with a sterile pastette to each sample, including the control samples. The samples are mixed thoroughly and left to stand for 5 minutes.
12. Using a sterile plastic pastette, "Growth Media" is added to the 5 ml graduation mark in each sample tube and the contents mixed and incubated for 4 hours at 35–37° C. without shaking.

Visualization of bacteriophage plaques:

13. Using a sterile plastic pastette, 1.0 ml of "Helper Cells" is added to each test and control sample.
14. 5 ml of molten base agar is added to each sample and the sample and agar mixed by gently swirling.
15. The contents of each tube are poured into a cooled correspondingly labelled "Indicator Plate".
16. The "Indicator Plates" are left on the bench for 30 minutes to let the agar solidify.
17. The "Indicator Plates" are held at 37° C. for 15 hours.
18. The number of plaques on each "Indicator Plate" is counted visually by observing the plate against a dark background. On the plates the growth of the "Helper Cells" is seen as an opaque area with areas of lysis due to bacteriophage being seen as clear or transparent areas within this turbidity (plaques).

Checking the control tubes:

Before analysing the results in the test samples, the in-activation control samples are examined for the occurrence of lysis by phage which have survived the in-activation treatment. There should be less than 10 plaques on this plate. If there are more than 10 plaques, then the chemical inactivation of exogenous phage was incomplete and the assay must be repeated. The positive control plate is examined for plaques. Extensive lysis should have occurred and there should be large numbers of plaques on this plate. In some circumstances, there may be no growth of "Helper Cells" at all due to complete lysis of the cells with the result that the plate may have no bacterial lawn.

Each of the test sample plates is examined and the presence of plaques or lysis is assessed according to the following criteria:

+++ Complete lysis, no bacterial debris
++ Complete lysis but some bacterial debris
+ Plaques merged but some individual plaques if the number of plaques can be counted record this number
− No plaques observed.

Those plates showing lysis indicate that those sputum samples contain viable mycobacteria which have hosted the replication of mycobacteriophage.

Eight decontaminated sputum samples from pulmonary tuberculosis patients were tested by the above phage assay technique which showed that five of the samples contained viable *Mycobacterium tuberculosis* and that three did not. When these results were compared with those obtained by conventional bacterial culturing of the samples, the five samples which were positive by culture were also positive by the phage assay, ie. supported survival and replication of the bacteriophage, whereas the three samples which were negative by culture were also negative by the phage assay, ie. did not support survival and replication of the bacteriophage.

The reagents used in the above test method were as follows:

Decontaminating Agent: 2 gms NaOH, 0.5% N-acetyl L-cysteine in sterile distilled water to 100 ml.
Growth Media: 7H9, OADC supplement with 0.1% glycerol.
Base agar: Growth media with 1.5% Bactoagar added
Bacteriophage: Bacteriophage D29 prepared from a plate lysate. A 90 mm petri dish showing confluent lysis was flooded with 10 ml 7H9, OADC, 0.1% glycerol, 1 mM $CaCl_2$ and left overnight (16 hours) in the fridge. The liquid was harvested from the plate using a pastet and centrifuged at 4000×g for 15 minutes. The supernatant liquor was filter sterilized through a 0.4 $\mu$ filter, aliquotted and stored at 4° C.
Helper Cells: *Mycobacterium smegmatis* grown to stationary phase and stored at 4° C.
Inactivating Reagent: 100 mM ferrous ammonium sulphate, filter sterilised.

EXAMPLE 4

The rationale of the invention was tested for drug susceptibility testing of Mycobacteria in a safe model system. BCG was used as the model for a susceptible Mycobacteria (susceptible to low concentrations of isoniazid and rifampicin) whereas *Mycobacterium smegmatis*, which is inherently resistant to isoniazid and partially resistant to rifampicin, was used as the model for resistant or semi-resistant Mycobacteria.

Step 1. A colony of BCG from an agar-based medium was grown in liquid culture in 7H9, OADC at 37° C. for two weeks to yield a stock of drug sensitive cells which could be used in the detection assay. Similarly a stock of *Mycobacterium smegmatis* was grown for 24 hours in 7H9, OADC to yield a stock of drug resistant cells. In the clinical situation these cells would originate directly from a clinical sample and would not require this pre-culture step. In the clinical situation the drug sensitive cells would be various strains or isolates of *Mycobacterium tuberculosis*.

Step 2. 100 $\mu$l of each culture was incubated for 72 hours with isoniazid and rifampicin at various concentrations in a volume of 3 mls 7H9, OADC. This step is necessary to allow the cells to be affected by the antibiotic drug. Controls containing no drug were also set up.

Step 3. 100 $\mu$l of each culture was then removed for testing.

Step 4. 800 $\mu$l of 7H9, OADC containing $5\times10^6$ D29 phage was added and incubated at 37° C. either for 4.5 hours for the BCG cultures or for 40 minutes for the *Mycobacterium smegmatis* cultures. Heat killed BCG and *Mycobacterium smegmatis* and phage only samples were also included in the experiment as controls.

Step 5. Exogenous phage were then in-activated by the addition of 100 $\mu$l acid buffer pH 2.2 (made by mixing 32.2 ml of 0.1M disodium citrate and 67.8 ml 0.1M HCl).

Step 6. After 5 minutes, 84 $\mu$l of 1.0M NaOH was added to neutralize the acidity.

Step 7. A further 4 mls of 7H9, OADC was added and the *Mycobacterium smegmatis* cultures were plated directly. The BCG cultures, however, were incubated at 37° C. for 3 hours to allow the endogenous, protected, phage to replicate within any live or viable cells.

Step 8. 100 $\mu$l of each culture was then mixed with 5 ml of fluid 7H9, OADC containing 5% (v/v) of a stationary phase *Mycobacterium smegmatis* culture and 0.7% Bactoagar (Difco) and poured into a 50 mm petri dish.

Step 9. After the agar had set, the plates were incubated at 37° C. for 16 hours. During this time any endogenous phage surviving the acid treatment in viable Mycobacteria replicated and lysed the original target cells and at least some of these phage established new replicative cycles within the rapid grower *Mycobacterium smegmatis* indicator cells.

Step 10. The plates were then observed for clear areas of phage lysis or plaques among the cloudy growth of uninfected indicator cells. The results were recorded and are shown below:

| | Isoniazid concentration (µg/ml) | | | Rifampicin Concentration (µg/ml) | | | no drug | no drug | Heat-Killed |
|---|---|---|---|---|---|---|---|---|---|
| | 0.1 | 1.0 | 10 | 10 | 50 | 100 | | | |
| M. tuberculosis | 122 | 40 | 2 | 4 | 4 | 10 | 71 | 109 | 1 |
| M. smegmatis | ++ | ++ | + | ++ | 50 | 8 | ++ | ++ | 1 |

This table shows the number of plaques observed with the different Mycobacteria grown in the presence of various antibiotics.

++ plaques merged with some growth of indicator cells between plaques

+ individual plaques observed but too many to count

The slow growing *Mycobacterium tuberculosis* is susceptible to isoniazid and rifampicin. When grown in the presence of rifampicin, the cells are killed and consequently there are no viable cells to protect the phage from inactivation and to support their growth. The numbers of plaques observed in the presence of all concentrations of rifampicin are not significantly above background levels; background being the number of plaques observed in the heat killed samples. The rapid grower *Mycobacterium smegmatis* is, however, resistant to low concentrations of rifampicin and this can be observed from the large numbers of plaques at the lowest rifampicin concentration. As the concentration of rifampicin is increased the cells are affected and there is a progressive reduction in the numbers of plaques.

The effect of rifampicin in Mycobacteria is known to be rapid, whereas isoniazid takes some time to exert its effect. Consequently, at the lowest concentration of isoniazid the BCG was unaffected and this was reflected in the number of observed plaques which was in the region of the numbers of plaques observed in the no drug controls. At higher concentrations of isoniazid, however, there was a marked reduction in the numbers of plaques reflecting the death of these cells. In contrast, the *Mycobacterium smegmatis* was mostly unaffected by isoniazid with only a slight reduction in the numbers of plaques at the highest concentration.

This experiment shows that this invention can be used to assess the drug susceptibility of a slow growing cell such as *Mycobacterium tuberculosis*. The assay is simple to perform, can be performed on small numbers of cells and the result is available within 4 days, which includes the time required to allow the drug to exert its effect on the cells. Conventional drug susceptibility assays using culture techniques need larger numbers of cells and can take up to 4 weeks to achieve a result. The Bactec system, which is more rapid than conventional culture techniques, requires a large item of expensive equipment, whereas the method of the invention needs the minimum of equipment, is inexpensive and more suited to the third-world environment where tuberculosis is more common.

Accordingly, the present invention also provides a method for assessing the effect of a treatment upon a bacterium, which method comprises:

i. exposing the bacterium to the treatment; and then ii. assessing the number of viable bacterium cells remaining in a sample of the bacterium by:

a infecting the sample of the treated bacterium with a phage infection to which the bacterium is permissive;

b in-activating the exogenous phage particles in the infected sample;

c cultivating the in-activated sample in the presence of a second bacterium which has a doubling rate greater than that of the first bacterium, and d assessing the extent of plaque formation and/or of second bacterium growth.

The method of the invention can also be used to assess the effect of a composition on a phage by:

a. treating the phage particles with the composition;

b. infecting a first bacterium permissive to the live phage with the treated phage particles;

c. in-activating the phage particles exogenous to the infected first bacterium cells;

d. cultivating the in-activated cells in the presence of a second bacterium which has a doubling rate greater than, preferably at least twice as great, typically 4 to 10 times greater, than that of the first bacterium; and e. assessing the extent of plaque formation and/or of second bacterium growth in the cultivated second bacterium cells.

In this application of the method of the invention, the extent of bacterial growth indicates the efficacy or otherwise of the initial treatment of the phage particles. If no plaques are formed, the initial treatment has killed or in-activated the phage particles and has thus prevented their infection of the first bacterium cells. The replication of these cells in the stage of cultivation of the second bacterium has not released phage particles which have killed or prevented replication of the second bacterium cells. The cultivated second cells will thus show substantially uniform colour or opacity indicating uniform growth of the bacterial cells. Where the composition has not been effective in killing or in-activating the phage particles, these will infect the first bacterium cells and will be protected against the in-activation treatment of the infected first bacterium. When the infected cells are cultivated in the presence of the second bacterium, the phage particles will replicate and lyse from the infected first cells to infect the second bacterium cells to give plaques or visibly uneven growth of the second bacterium. The extent of the plaques or uneven growth gives an indication of the number of phage particles present and hence the extent of the efficacy of the initial treatment on the phage particles. Whilst this application of the method of the invention may not give quantitative results, it provides a rapid initial screening technique which can be used to discriminate between potential candidate compositions which can then be subjected to other tests to determine the quantitative effect of the compositions.

Accordingly, in its broadest aspect, the present invention provides a method for enhancing the time of response of an assay for a first bacterium, characterised in that:

a. the said first bacterium is exposed to infection by phage particles to which the said first bacterium is permissive;

b. the infected bacterium is treated to in-activate exogenous phage particles;

c. the treated bacterium is cultivated in the presence of a second bacterium which is also permissive to the said phage or its replicand and which has a doubling rate greater than, preferably at least twice as great, typically 4 to 10 times greater, than the effective doubling rate of the first bacterium; and d. assessing the extent of plaque formation and/or of second bacterium growth in the cultivated second bacterium cells.

I claim:

1. A method for reducing the time of response of an assay for a first bacterium, wherein:
   a) the first bacterium is exposed to infection by phage particles to which said first bacterium is permissive;
   b) the infected bacterium is treated to inactivate exogenous phage particles;
   c) the treated bacterium is cultivated in the presence of a second bacterium which is permissive to said phage or its replicand and which has a doubling rate greater than the effective doubling rate of the first bacterium; and
   d) assessing the extent of plaque formation and/or of second bacterium growth in the cultivated second bacterium cells.

2. A method as claimed in claim 1, wherein said method provides a method for detecting the presence of a first bacterium in a sample, which method comprises the steps of:
   a) infecting a viable sample of the first bacterium cells with a phage which is specific to that bacterium whereby at least some of the bacterium cells each absorb one or more of the phage particles;
   b) inactivating or removing the phage particles which have not been absorbed by the bacterium cells;
   c) cultivating the infected first bacterium cells in a medium containing at least one other second bacterium which has a doubling rate greater than the effective doubling rate of said first bacterium, whereby at least some of the said second bacterium cells become infected by phage particles released upon the lysis of said infected first bacterium cells, each of said infected bacterium cells acting as a source for further infection of a subsequent generation of the infection cycle; and
   d) monitoring the population of phage particles and/or the reduced growth of the said second bacterium in step c) to determine the presence of said first bacterium cells in the sample under test.

3. A method as claimed in claim 1, wherein said method provides a method for estimating the effect of a virus growth regulating composition or of a virucide composition on particles of a phage by assessing the ability of the phage particles in replicating in a bacterial cell, which method comprises the steps of treating the phage particles with the composition, and
   a) infecting a first bacterium permissive to the live phage with the treated phage particles;
   b) inactivating the phage particles exogenous to the infected first bacterium cells;
   c) cultivating the infected first bacterium cells in the presence of a second bacterium which has a doubling rate greater than the effective doubling rate of the first bacterium;
   d) assessing the extent of plaque formation and/or of second bacterium growth in the cultivated second bacterium cells; and
   e) correlating (i) the extent of plaque formation and/or of second bacterial growth with (ii) the extent of plaque formation and/or second bacterial growth in the absence of the virus growth regulating composition or virucide, to estimate the effect of the virus growth regulating composition or virucide on the phage particles.

4. A method as claimed in claim 1, wherein said method provides a method for assessing the effect of a treatment upon a bacterium, which method comprises:
   i) exposing the bacterium to the treatment; and then
   ii) assessing the number of viable bacterium cells remaining in a sample of bacterium by:
      a) infecting the sample of the treated bacterium with a phage infection to which the bacterium is permissive;
      b) inactivating the exogenous phage particles in the infected sample;
      c) cultivating the inactivated sample in the presence of a second bacterium which has a doubling rate greater than the effective doubling rate of the first bacterium;
      d) assessing the extent of plaque formation and/or of second bacterium growth; and
      e) correlating (i) the extent of plaque formation and/or of second bacterial growth with (ii) the extent of plaque formation and/or second bacterial growth in the absence of the treatment of bacterium in step i), to estimate the effect of the treatment on the bacterium.

5. A method as claimed in any one of claims 1 to 4, wherein the first bacterium has an effective doubling rate which is greater than 10 hours at 37° C. in a culture medium comprising 90% v/v of the medium known as 7H9 and 10% v/v of the nutrient known as OADC.

6. A method as claimed in any one of claims 1 to 4 wherein the second bacterium has a doubling rate which is at least twice as great as the effective doubling rate of the first bacterium.

7. A method as claimed in claim 6, wherein the second bacterium has a doubling rate which is 4 to 10 times greater than the effective doubling rate of the first bacterium.

8. A method as claimed in claim 7, wherein the first bacterium is a Mycobacterium spp or a Legionella spp.

9. A method as claimed in claim 8, wherein the first bacterium is *Mycobacterium tuberculosis.*

10. A method as claimed in claim 8, wherein the second bacterium is *Mycobacterium smegmatis.*

11. A method as claimed in any one of claims 1 to 4, wherein the first bacterium has an effective doubling rate of from 2 to 10 hours.

12. A method as claimed in claim 1, wherein the infection of the first bacterium with the phage particles is carried out at a temperature up to 55° C. and for a period of from 10 minutes to 4 hours.

13. A method as claimed in claim 1, wherein the phage is AG1, B1, $BG_1$, $BK_1$, C3, D29, D34, D56A, GS4E, HP1, L1, I3 or TM4.

14. A method as claimed in claim 1, wherein the first bacterium is *Mycobacterium tuberculosis,* the second bacterium is *Mycobacterium smegmatis* and the phage is D29 or TM4.

15. A method as claimed in claim 1, wherein the exogenous phage particles are inactivated in step b) by:
   i) washing and filtration of the infected bacterial material to separate the exogenous phage particles from the infected first bacterium cells; or
   ii) treatment of the infected first bacterium material with a virucide, an acid or a surfactant to kill or render inactive the exogenous phage particles; and/or
   iii) preferentially absorbing the exogenous phage particles from the first bacterial material onto a substrate which is separated from the bacterial cells.

16. A method as claimed in claim 1, wherein the second bacterium is provided in an initial amount in step c) so as to provide from 2 to 50 times the number of first bacterium cells in the mixture of infected first bacterium and second bacterium to be cultivated.

17. A method as claimed in claim 1, wherein the cultivation step c) of the method is carried out until a the steady state at which further bacterial cell growth and lysis ceases is reached.

18. A diagnostic kit for use in the method of claim 1 to detect the presence or absence of a first bacterium in a sample, wherein the kit comprises:

i) a source of a known phage infection for the first bacterium; and ii) a source of a viable second bacterium which has a doubling rate which is greater than that of the first bacterium and which is permissive to the phage particles to be released from the first bacterium infected by said phage infection.

19. A diagnostic kit as claimed in claim 18, wherein the kit further comprises means for inactivating and/or removing the exogenous phage particles from first bacteria infected by said source of phage infection.

20. A method as claimed in claim 8, wherein the first bacterium is *Mycobacterium avium*.

21. A method as claimed in claim 8, wherein the second bacterium is *Mycobacterium aurum*.

22. A method as claimed in claim 1, wherein the first bacterium is *Mycobacterium avium*, the second bacterium is *Mycobacterium smegmatis* and the phage is D29 or TM4.

\* \* \* \* \*